United States Patent [19]

McElroy et al.

US005674713A

[11] Patent Number: 5,674,713

[45] Date of Patent: Oct. 7, 1997

[54] DNA SEQUENCES ENCODING COLEOPTERA LUCIFERASE ACTIVITY

[75] Inventors: Marlene DeLuca McElroy, deceased, late of La Jolla, by W. D. McElroy, executor; Donald Raymond Helinski, La Jolla; Keith Vernon Wood, San Diego; Jeffrey Roux De Wet, Menlo Park; David Wing Ow, San Francisco; Stephen Herbert Howell, Del Mar, all of Calif.

[73] Assignee: The Regents of the University of California, Oakland, Calif.

[21] Appl. No.: 460,214

[22] Filed: Jun. 2, 1995

Related U.S. Application Data

[62] Division of Ser. No. 60,091, May 10, 1993, which is a continuation of Ser. No. 792,644, Nov. 15, 1991, abandoned, which is a continuation of Ser. No. 119,096, Nov. 10, 1987, abandoned, which is a continuation-in-part of Ser. No. 803,820, Dec. 2, 1985, abandoned.

[51] Int. Cl.⁶ .................. C12N 1/21; C12N 5/10; C12N 15/53; C12N 9/02
[52] U.S. Cl. ............. 435/69.7; 435/6; 435/189; 435/240.1; 435/252.3; 536/23.2; 536/23.4
[58] Field of Search .................. 435/172.3, 320.1, 435/320.3, 240.1, 240.2, 69.7, 189, 6; 536/23.2, 23.4

[56] References Cited

U.S. PATENT DOCUMENTS

| | | | |
|---|---|---|---|
| 4,581,335 | 4/1986 | Baldwin | 435/172.3 |
| 4,604,364 | 8/1986 | Kosak | 436/501 |
| 4,968,613 | 11/1990 | Masuda et al. | 435/172.3 |

FOREIGN PATENT DOCUMENTS

| | | |
|---|---|---|
| 3314812 | 10/1984 | Germany. |
| 8400774 | 3/1984 | WIPO. |

OTHER PUBLICATIONS

Alter et al., *Biochemistry*, 25, 1599–1605 (1986).
Baughman et al., *Virology*, 167, 125–135 (1988).
Belas et al., *J. Bacteriology*, 158, 890–896 (Jun., 1984).
Borror et al., *An Introduction to the Study of Insects*, 67–68 (1976).
Cohn et al., *J. Biological Chemistry*, 260, 10, 6139–6146 (May 25, 1985).
DeLuca et al., *Bioluminescence and Chemiluminescence: Basic Chemistry and Analytical Applications*, 215–222 (1981).
De Wet et al., *DNA*, 3, 6, 437–447 (1984).
De Wet et al., *Proc. Natl. Acad. Sci. USA*, 82, 23, 7870–7873 (Dec., 1985).
De Wet et al., *Methods in Enzymology*, 133, 3–11 (1986).
De Wet et al., *Molecular and Cellular Biology*, 7, 2, 725–737 (Feb., 1987).
Dunlap et al., *Journal of Bacteriology*, 164, 1, 45–50 (Oct., 1985).
Engebrecht et al., *Cell*, 32, 773–781, (Mar., 1983).
Engebrecht et al., *Methods in Enzymology*, 133, 83–96 (1986).
Gelmini et al., *Bioluminescence and Chemiluminescence: Status Report*, (Proc. of Vith Int'l. Symp. on Biolum. and Chemilum., 200–205, (1993).
Haenggi et al., *Chem. Abst.*, 102, 361, Abst. No. 20786p (1985) [This is the Same as the German Reference to Battelle].
Hastings, *J. Mol. Evol.*, 19, 309–321 (1983).
Lee et al., *Biochemistry*, 20, 1253–1256 (1981).
Luehrsen, et al., *Methods in Enzymology*, 216, 397–414 (1992).
Maniatis et al., *Molecular Cloning: A Laboratory Manual*, 212–216 (1982).
McElroy et al., *Chemi- and Bioluminescence*, 387–399 (1985).
McElroy et al., *Bioluminescence in Action*, 109–127 (1978).
McElroy et al., *Chemiluminescence and Bioluminescence*, 285–311 (1973).
McElroy et al., *Molecular Architecture in Cell Physiology*, 63–80 (1966).
Miyamoto et al., *Methods in Enzymology*, 133, 70 (1986).
Nilsson et al., *Immobilization and Purification of Enzymes with Staphylococcal Protein a Gene Fusion Vectors*, 1075–1080.
Okayama et al., *Molecular and Cellular Biology*, 3, 2, 280–289 (Feb., 1983).
Ow et al., *Science*, 234, 856–859 (Nov. 14, 1986).
Ow et al., *Proc. Natl. Acad. Sci. USA*, 84, 4870–4874 (Jul., 1987).
Reil et al., *Biochimica et Biophysica Acta*, 1050, 288–292 (1990).
Saviranta et al., *Bioluminescence and Chemiluminescence: Status Report*, (Proc. of Vith Int'l. Symp. on Biolum. and Chemilum.: 1993), 94–98.
Schölmerich et al.(Eds.), *Bioluminescence and Chemiluminescence: New Perspectives*, (Proc. of Ivth Int'l. Biolum. and Chemilum. Symp.: 1986), VII–XIII.
Tatsumi et al., *Journal of Bioluminescence and Chemiluminescence*, 3, 75–78 (1989).
Ward, *Chemi –and Bioluminescence*, 321–358 (1985).
Wienhausen et al., *Photochem. and Photobiol.*, 42, 5, 609–611 (1985).
Wood et al., *Biochemical and Biophysical Communications*, 124, 2, 592–596 (1984).
Wood et al., *Science*, 24, 700–702 (May 12, 1989).
Young et al., *Proc. Natl. Acad. Sci. USA*, 80, 1194–1198 (Mar., 1983).

*Primary Examiner*—John L. LeGuyader
*Attorney, Agent, or Firm*—Brown, Martin, Haller & McClain

[57] ABSTRACT

DNA compositions and methods of constructing and using the same consisting of DNA sequences encoding luciferase activity, or DNA sequences encoding hybrid molecules exhibiting luciferase activity and a second biological activity that are useful in performing biological assays.

17 Claims, 5 Drawing Sheets

5,674,713

DNA SEQUENCES ENCODING COLEOPTERA LUCIFERASE ACTIVITY

This is a divisional of application Ser. No. 08/060,091, filed May 10, 1993, which is a continuation of 07/792,644, filed Nov. 15, 1991, now abandoned, which is a continuation of 07/119,096, filed Nov. 10, 1987, now abandoned, which is a continuation-in-part of 06/803,820, filed Dec. 02, 1985, now abandoned.

This invention was made with Government support under Grant No. PCM 8305446 with the National Science Foundation and Grant No. AI-07194 with the United States Department of Health and Human Services and the University of California. The Government has certain rights in this invention.

BACKGROUND OF THE INVENTION

A large repertoire of assay methods are available for determining the presence of naturally occurring or synthetic molecules in biological fluids. Thus it is commonplace in a commercial or academic laboratory for one to employ a battery of cytochemical, immunochemical, radiochemical and physical chemical assays, or variations thereof, where detection of the substance of interest is premised on specific recognition by antibody, enzymatic reactions, viscosity changes, etc. Particularly popular are immunochemical assays reliant on antibody/antigen complex formation, and either radiometric or colorimetric detection of the complex.

Associated with each type of assay are advantages and disadvantages that are uniquely characteristic of that particular assay. For instance, radiochemical-based assays exhibit high sensitivity, yet present significant handling and storage problems. In contrast, the opposite is generally true for nonradiochemical-based assays; that is, they are less sensitive but do not have the handling and storage problems of radiochemical assays. Because of the problems associated with radiochemical assays, considerable effort has been expended in order to develop assays as sensitive as radiochemical assays but without their drawbacks.

Bioluminescent assays theoretically offer the sensitivity of radiochemical assays but without the attendant problems; however, for several reasons they have not been widely utilized. Most such assays are based on light emission effected by the catalytic activity of luciferase with luciferin in the presence of ATP and molecular oxygen. The reaction consists of the conversion of luciferin to oxyluciferin with the concomitant generation of light. Thus, in lieu of using radio tracers, luciferase can be covalently attached to a ligand and then employed in any number of competitive binding assays. Nearly all bioluminescent assays employ luciferase isolated from either insects or bacteria, and luciferase from the bacterium *Vibrio fischeri* has recently been cloned. This bacterial luciferase consists of two different subunits. Because of its higher quantum efficiency and single subunit structure, insect luciferase is preferred over the multisubunit bacterial luciferase.

Unfortunately, there at least two problems associated with bioluminescent assays. First, luciferase is not readily available and easily isolated; and, second, the enzyme is easily denatured and hence rendered inactive by the chemical reactions necessary to effect covalent attachment to a ligand.

SUMMARY OF THE INVENTION

The invention involves cloning and expressing regions of DNA that encode enzyme molecules with bioluminescence activity. The invention makes possible the isolation of a bioluminescent reporter molecule, luciferase, useful in virtually all biological assays, and additionally permits the molecular construction of dual-function hybrid molecules. The hybrid molecules obtained uniformly exhibit luciferase activity plus a second biological activity.

In one aspect, the invention is a method for producing hybrid molecules useful in biological assays exhibiting luciferase activity and a second functionality, comprising: forming an association of three sequences of DNA by isolating a first sequence of DNA encoding luciferase activity, and associating with said first sequence of DNA a second sequence of DNA encoding said second functionality; associating said first and second sequences of DNA with a third sequence of DNA encoding functions allowing for selecting, replicating, and expressing said hybrid molecules in a suitable host cell; inserting said association of three sequences of DNA into said suitable host cell; selecting and replicating said host cells; and isolating from said host cells said hybrid molecules.

In another aspect, the invention is a hybrid plasmid, comprising: a first DNA sequence for encoding a biological molecule exhibiting luciferase activity; a second DNA sequence encoding a biological molecule lacking luciferase; and a third DNA sequence for encoding functions allowing for selecting replicating, and expressing said plasmid in a suitable host cell.

In yet another aspect, the invention is an immunoassay method for determining the concentration of antigenic substances in fluids, comprising the steps of: affixing antibodies directed against antigenic determinants of said antigenic substances to a solid surface; forming a mixture by contacting said solid surface in an aqueous solution containing fluid with an unknown amount of said antigenic substances and a hybrid molecule exhibiting at least one of said antigenic determinants of said antigenic substances and luciferase activity; incubating said mixture under conditions of controlled time, temperature, pH, and concentration of said antibody bound to said solid surfaces to allow bonding of said antigenic substances and said hybrid molecules to said antibody; separating said solid surfaces containing bound antigenic substances and hybrid molecules; and determining the intensity of bioluminescence emitted from said hybrid molecules bound to said solid surfaces and comparing that intensity with the intensity from a mixture of incubation containing a known concentration of said antigenic substances.

Numerous other aspects are closely related and are described herein and reflected in the appended claims.

DETAILED DESCRIPTION OF THE INVENTION

Figure 1:
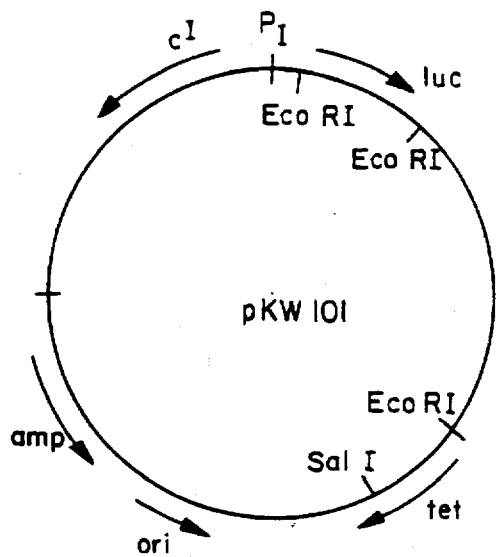
FIG. 1 is a schematic diagram of the essential features of the plasmid pKW101.
Figure 13:
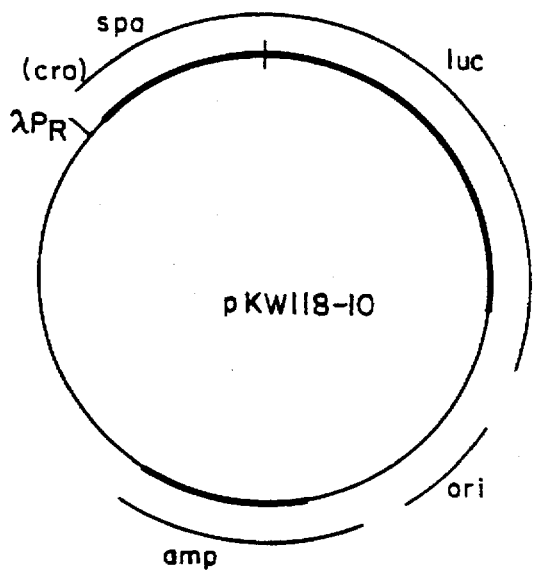
FIG. 13 is a schematic diagram of the plasmid pKW118-10.

The bioluminescence assay of the subject invention involves cloning and expressing a region of DNA that encodes a single protein subunit with luciferase activity, and then combining this region with other regions of DNA in suitable expression systems to produce hybrid molecules useful in a variety of biological assays. Cloning of DNA sequences that encode luciferase activity can be accomplished by constructing either a cDNA or genomic library from an organism that exhibits such activity. Particularly useful for making a cDNA or genomic library is mRNA or DNA, respectively, isolated from the firefly *Photinus pyralis* but it is to be anticipated that other insect species or worms that display the phenomena of bioluminescence can be suitably employed. Examples are Lampyridae, Elateridae, or Diptera.

Generation of a cDNA library is realized by isolating mRNA, particularly poly (A)⁺RNA, by techniques well-known to those in the art, for example by chromotography on oligo [dT]-cellulose as described by Aviv and Leder in *Proceeding of the National Academy of Sciences, U.S.A.* (1972, Vol. 69, No. 6:1408–1412), and reverse transcribing the poly (A)⁺RNA into cDNA. The cDNA can then introduced into a suitable cloning vector and either transformed or transfected into procaryotic or eucaryotic cells. Any one of a number of vectors can be employed, including plasmids, cosmids, viral vectors or hybrids thereof.

The general scheme for generating a cDNA library is to insert double-stranded cDNA made from mRNA into a suitable vector. This is conveniently accomplished by inserting the cDNA into a cloning site near a functional promoter and a translational initiation site on a suitable vector. This favored cloning site is present within the coding region of genes present on *Escherichia coli* plasmids or bacteriophages. Several examples are well-known, particularly the β-lactamase gene of pBR322, the β-galactosidase (Lac Z) gene of pUC plasmids and gt11, and the tryp genes of the tryptophan promoter plasmids. The insertion of cDNA results in a hybrid molecule, or fused polypeptides consisting of the NH2-terminal region of an *E coli* protein covalently linked to a polypeptide and coded by the cloned cDNA fragment. If there are no "stop signals" separating the inserted cDNA fragment with the bacterial translation initiation signals, the hybrid RNA transcript is translated in the same "reading frame" as in the original mRNA. The fused molecule is then amenable to detection in cells that harbor the vector using a variety of immunochemical or radiochemical nucleotide hybridization techniques.

Regardless of which vector is chosen to clone cDNA sequences encoding luciferase activity, it is necessary to select those cells that receive the vector from those that do not. In this regard, gt11, a procaryotic expression vector described by Young and Davis in *The Proceeding of the National Academy of Science* (Mar. 1983, 80: 1194–1198), is attractive because it permits the construction and maintenance of large cDNA libraries, and ready detection of cells harboring cDNA regions with luciferase activity. In the gt11 system, double-stranded cDNA produced from mRNA isolated from bioluminescent insects is inserted into the restriction endonuclease Eco RI site in the *E coli* Lac Z (β-galactosidase) gene carried by gt11. This requires revealing ligation compatible nucleotide sequences on both the cDNA and gt11 DNA to effect covalent bond formation between the two. Generally, this can be realized by ligating Eco RI restriction endonuclease linkers to cDNA fragments and treating gt11 with Eco RI prior to inserting the cDNA into the phage. Lastly, gt11 containing foreign cDNA inserts is packaged in vitro to yield infectious phage particles and infected into a compatible strain of bacteria. After amplifying the cDNA library, gt11 phage that harbor DNA sequences encoding luciferase activity are identified by plating recombinant phage on a lawn of *E. coli* and inducing the production of hybrid proteins having luciferase and β-galactosidase sequences by adding an inducer of Lac Z transcription. The inducer enhances the level of hybrid protein production and therefore enhances the sensitivity of detecting cells harboring DNA sequences encoding luciferase antigenic activity. In many instances, addition of inducer will not be necessary as the level of hybrid protein production will be sufficiently great to be detected without its addition. A suitable inducer is isopropylthio-β-D-galactopyranoside (IPTG).

Lac Z transcription directs the expression of foreign DNA inserts, that is proteins with luciferase properties. The latter are screened for luciferase antigenicity with antibody directed against luciferase by incubating the *E. coli* with antibody for a period of time sufficient to allow antibody binding to luciferase determinants. After a wash step to remove unbound antibody, bound luciferase antibody can be revealed by several techniques, one being to incubate the gt11-infected antibody-treated lawn of *E. coli* with labeled-protein A of *Staphylococcus aureus* or a second antibody directed against the luciferase antibody molecule. The second antibody carries a suitable reporter molecule, such as radioactive atoms or enzyme molecules.

A variety of radioactive and enzymatic reporter molecules, or complexes thereof, are available for use with the second antibody, examples being radioactive iodine and the enzyme peroxidase. After allowing sufficient time for the second antibody to react with bound luciferase antibody, the lawn of cells is washed, and bound antibody revealed either by radioautography if radioactive atoms are used, or by the addition of a suitable chromogenic peroxidase substrate, particularly 4-chloro-1-naphthol if peroxidase is utilized. The latter is dissolved in a suitable solvent, methanol being effective, and then added to an aqueous solution containing $H_2O_2$. While the amount of the various substances can vary significantly without the detection of bound antibody being adversely affected, for optimal resolution about 60mg of 4-chloro-1-naphthol is dissolved in 20ml of methanol, which is added to 100ml of an aqueous solution containing 60ul of 30% $H_2O_2$. Those gt11 recombinant plaques exhibiting luciferase antigenicity exhibit a purple color.

In addition to the aforementioned ways of detecting bound luciferase antibody, an alternate technique may be used that involves screening the cDNA library with a biotin-labeled second antibody, and subsequent formation of biotin-avidin peroxidase complex that is revealed by hydrolysis of a chromogenic peroxidase substrate. A suitable substrate is diaminobenzidine. This procedure is faster, requiring four hours to ascertain a positive plaque.

Luciferase antibody can be generated in rabbits as described by Green and McElroy in *Biochemical Biophysical Acta* (1956, 20:170–178) using purified firefly luciferase or by generating murine monoclonal anti bodies against luciferase by the procedure of Kohler and Milstein as described in *Nature* (1975, 256:495–497), and Dosch and Gelfand in *The Journal of Immunology* (1977, 118:302–308). The latter references describes a procedure whereby murine monoclonal antibodies can be generated in vitro Additionally, human monoclonal antibodies can also be produced by in vitro immunization techniques as described by Boss in *Brian Research* (1984, 291:193–195). In the case of rabbit serum containing luciferase antibodies, it is often necessary to separate from these antibodies other antibody populations that recognize *E. coli* or phage antigenic determinants, as well as luciferase antibodies that may cross-react with *E. coli* or phage. This can be accomplished by absorption of the undesirable substances to *E. coli* or phage using techniques described by de Wet et al. in *DNA* (1984, Vol 3, No. 6:437–447).

The gt11 cDNA inserts were isolated prior to identifying those that encode molecules with luciferase activity in a suitable expression vector and to constructing plasmids useful to express hybrid proteins. This was accomplished by isolating plaques that exhibit luciferase antigenicity, and the recombinant phage amplified by infecting a suitable strain of *E. coli*. DNA from recombinant gt11 phage was isolated from the desired plaque by one of several techniques, one being to isolate phage DNA from plate lysates performed as described in Maniatis, Fritsch, and Sandbrook in *Molecular Cloning* (1982, Cold Spring Harbor Laboratory, Cold Spring Harbor, New York, pp. 371–372). Isolated recombinant phage DNA was then cut with Eco RI to release cDNA inserts. The latter were purified preparative to inserting the cDNA fragment into a suitable expression vector. Several methods can be used to purify the restriction fragment; particularly convenient is the use of agarose gel electrophoresis onto a suitable paper substrate as described by Maniatis et al., supra.

To determine DNA inserts that encode protein with luciferase antigenic activity also exhibit luciferase enzymatic activity, cDNAs of various sizes were inserted into a host cell by transformation into procaryotes or transfection into eucaryotes, or into a suitable expression vector followed by transformation or by transfection. The latter procedure is more efficient and thus favored. A wide variety of procaryotic and eucaryotic vectors or "shuttle" vectors are routinely used for this purpose. The latter vectors are capable of replicating in both procaryotes and eucaryotes, as described by Struhl, Stinchcomb, Scherer, and Davis in *Proceedings of the National Academy of Sciences*, U.S.A. (1979, 76:1035–1039) A general description of expression vectors and methods of using and isolating the same can be found by Grover in *DNA Cloning*, Volume II, *A Practical Approach* (1985, IRL Press, Oxford, Washington, D.C.) or by Maniatis et al., supra.

It is to be anticipated that cDNA inserts obtained from gt11, or other vectors used to construct the initial gene library that encode protein with luciferase antigenicity, will be of varying size. Moreover, it is to be further anticipated that a number of different sized inserts may exhibit luciferase enzymatic activity. Regardless of the size of the insert, it can be assayed for luciferase activity and used to produce molecules with luciferase alone, or to construct hybrid molecules exhibiting luciferase activity and antigenic and/or enzymatic activity. Regardless of cDNA size, cDNA expression is assayable by inserting the cDNA so as to come under the transcriptional and translational control mechanisms of either the vector employed and/or the host cell chosen to carry the vector. This procedure may require inserting suitable "linkers" into either the vector, the cDNA, or both. In addition to obtaining cDNA fragments that encode luciferase activity by excision from the vector initially used to produce the gene library, it may be desirable in certain instances to reduce the size of such cDNAs by restriction endonuclease or exonuclease treatment with one or more enzymes. As described above, these fragments can similarly be inserted into a suitable expression vector.

After inserting cDNAs exhibiting luciferase antigenic activity into suitable expression vectors, the expression product can be tested for luciferase enzymatic activity by preparing an extract of cells containing the cDNA insert, and adding to the extract the necessary co-factors to produce bioluminescence. Generally, this assay is performed in a buffered solution at near neutral pH containing magnesium chloride, luciferin and adenosine triphosphate. Light emission was detected with a luminometer.

In addition to ascertaining DNA sequences that encode luciferase activity by generating a cDNA library, it is possible to discern such sequences by constructing a genomic DNA library. This is accomplished by isolating DNA from a suitable bioluminescent insect or worm, particularly *P. pyralis*, and then fragmenting the DNA into fragments that are up to 20 kilobases long. This can be accomplished by using one or more restriction endonucleases followed by ligating the fragments into a suitable vector at a restriction site as described for generating a cDNA library. A useful restriction endonuclease is Sau3A, which yields 12 –20 kilobase DNA fragments when the DNA is partially digested.

While digestion with DNA restriction endonucleases allows for ready cloning of the fragments, and thus is the preferred method of fragmenting insect DNA, it is possible to obtain fragments by subjecting DNA to destructing forces, particularly sonication or mechanical agitation. The size of the DNA fragments dictates the ease and convenience of cloning; and while there is anticipated to be a lower upper limit comprising a DNA sequence that encodes luciferase activity, it appears that a fragment in the range of about 20 kilobases or less will dictate the type of cloning system employed.

Cloning of genomic DNA fragments to produce a genomic DNA library can be effected in a variety of plasmids, cosmids, vital vectors or hybrids thereof, similar to those used to produce a cDNA library. Vectors capable of replicating in either procaryotes, eucaryotes or both, that is shuttle vectors, are similarly utilized to generate a genomic library. Shuttle vectors are the preferred recipients of the DNA fragments as they permit growing the vector in usable quantities in bacteria, and then testing for the presence of the desired DNA sequence in eucaryotes. Regardless of the vectors used, all should contain one or more selectable markers. After DNA fragments are inserted into a suitable vector and the vector inserted into a host cell and the latter selected onto identified cells containing inserts, the genomic library is amplified and cells harboring DNA luciferase sequences identified. This can be achieved using immunochemical antibody detection techniques if the sequences are inserted into vectors compatible with such screening, such as pUC plasmids, gt11 or the like. Alternatively, DNA luciferase sequences can be ascertained using tracer-labeled homologous nucleotide probes. The latter can be generated by a variety of techniques well-known to those skilled in the art, particularly $^{32}P$ nick-translation techniques of cDNA-cloned probes with luciferase sequences, or by synthesizing an oligonucleotide probe homologous to luciferase DNA sequences. The latter probes are derived from a knowledge of luciferase immunoacid sequences translatable into nucleotide sequences via the genetic code. In addition other less convenient techniques are available for defining genomic DNA sequences such as employing labeled luciferase mRNA. Once cells are identified that harbor a recombinant vector exhibiting DNA luciferase sequences, the DNA from these structures can be isolated by techniques well-known in the art.

It should be noted that while cloning of either cDNA or genomic DNA sequences with luciferase activity can be readily achieved in *E. coli*-based plasmids or their phage, a variety of other vectors are usable and may even be preferred. For example, Mizamoto, Smith, Farrell-Towt, Chizzonite, and Summers in *Molecular and Cell Biology* (1985, 5:2860–2865) have shown that a baculovirus vector produces high levels of foreign protein in an insect cell line. Thus, since one possible luciferase that can be cloned by the methods of the subject invention is obtainable from insects, DNA sequences encoding the latter may be more stable in this system.

Regardless of whether a cDNA or genomic library is used to identify DNA sequences that encode luciferase activity, DNA inserts can be isolated from either library and used by themselves or in combination to construct expression vectors that produce hybrid molecules, particularly proteins that exhibit both luciferase activity and a second functionality. This can be accomplished by isolating the cDNA or the genomic DNA inserts and ligating either into a suitable expression vector at a site near a functional promoter and a translational initiation site on the promoter. The latter, of course, exhibits cell-selectable markers, as well as the necessary replication and regulation features associated with growing such vectors and expressing DNA inserts contained therein. Examples of such are genes that code for drug resistance or enhance upstream activation sites (UASs), as well as transcriptional control units that are not found on the upstream, i.e., the 5', side of the genes regulated. Additionally, once a vector has been obtained that contains either a cDNA or genomic DNA fragment or hybrid thereof that encodes or expresses luciferase activity, the DNA sequence can be mutated using a variety of techniques and chemicals to yield chemicals with altered luciferase activity. This can be accomplished by techniques well-known in the art, particularly those described by Smith in *The Annual Review of Genetics* (1985, pp. 423–462). Thus, DNA can be deleted from either the 5' or the 3' ends of the molecule, or mutagens such as sodium bisulfite can be employed. Following selection of cells harboring the mutant molecules, the latter can be isolated and assayed for features not associated with native luciferase. Such might be altered specificity for ribonucleoside triphosphates. Native luciferase utilizes adenosine triphosphate, and it can be expected that the molecule exhibiting guanosine triphosphate hydrolysis specificity will be obtained. Additionally, mutant molecules that exhibit altered light emission properties can also be expected to be produced by these techniques.

In addition to inserting cDNA, genomic DNA or hybrids constructed thereof encoding luciferase activity into bacteria or eucaryotic cells by expression vectors, the same can also be inserted into plants by one of two routes. First, a variety of vectors primarily based on Ti plasmids isolated from the bacteria *Agrobacterium tumefaciens* can be utilized. This involves inserting DNA sequences encoding luciferase activity downstream of a suitable plant cell promoter, transforming the bacterium with the recombinant plasmid, and then infecting plant cells with the bacterium. The most commonly used plasmids are the octopine or nopaline types. This procedure is preferred for dicotyleydonous species. The types of vectors available, including shuttle vectors, as well as their properties are described in An, Watson, Stachel, Gordon, and Nester in *The Journal of the European Molecular Biological Organization* (1985, 4:277–286); Caplan, Herrera-Estrella, Inze Van Haute, Van Montague, Schell, and Zambryski in *Science*(1984, 18:815–821); Fraley et al. in *Biotechnology* (1985, 3:629–635 and Klee, Yanofsky, and Nester in *Biotechnology* (1985, 3:637–642).

A second method for transferring DNA sequences encoding luciferase is to electroporate vectors containing the same directly into plant cells. This procedure complements Agrobacterium invection as it permits the transformation of monocotyledonous plant species.

The production of recombinant vectors that express molecules with luciferase activity and/or hybrid molecules that exhibit luciferase activity and a second biological activity are useful in a variety of biological assays. For example, luciferase can be employed to measure the amount of biomass present in a self-propagating system as described by De Luca and McElroy in *Methods in Enzymology* (1978, Academic Press, New York, 57:3–15).

Hybrid molecules exhibiting luciferase activity and a second protein capable of binding to cell associated cytoplasmic or plasma membrane structures can be expected to be favorably employed in a variety of cytochemical assays. For instance, it is possible to construct an expression vector exhibiting sequences that encode the antibody binding site of Protein A as the latter are described by Colbert, Anilionis, Gelep, Farley, and Breyer in *Journal Biological Response Modifiers* (1984, 3:235–259), and using the same in combination with DNA sequences encoding luciferase activity to produce a hybrid molecule with bioluminescence and antibody binding activity. Thus, using routine biochemical materials and methods, it is possible to use hybrid molecules exhibiting luciferase activity and Protein A binding activity to detect cell surface or cytoplasmic antibody via the Protein A antibody binding portion of the molecule, and detecting the amount bound, or the cell types that exhibit binding, by assaying for bioluminescence emitted by the luciferase active portion of the molecule in the presence of its requisite substrates.

Construction of hybrid molecules exhibiting luciferase activity and a second biological activity permit the use of the same in a wide variety of immunochemical, cytochemical, etc., assays. For instance, antibodies can be raised against the nonluciferase region of the molecule and used in standard solid or liquid phase immunoassays to detect the presence of molecules with similar antigenicity biological fluids. In this instance, detection and quantitation of the latter would be based on the intensity of light emission from the luciferase portion of the hybrid molecules.

EXAMPLES

Example 1

Construction of cDNA Library from *P. pyralis*.

Preparatory to creating a cDNA library, total RNA was isolated from the lanterns of fireflies, *P. pyralis*. The tissue was homogenized in guanidinium thiocyanate, and the RNA pelleted through a cesium chloride cushion as described by Chirgwin, Przbyal, MacDonald, and Rutter in *Biochemistry* (1979, 18: 5294–5298). Poly (A)⁺RNA was isolated by chromotography on oligo(dT)-cellulose as described by Aviv and Leder in *Proceedings of the National Academy of Science, U.S.A.* (1972, 69:1408–1412). Next the poly(A)⁺ RNA was eluted from the column with water and then precipitated with 1/10 volume of 3 molar sodium acetate and 2.5 volumes of ethanol were added. The RNA was precipitated overnight at _20° C. and pelleted. The pellet was washed with 70% ethanol, lyophilized, and the poly (A)⁺ RNA was dissolved in water and frozen.

The poly (A)⁺ RNA was used to generate cDNA as described by Maniatis, Fritsch, and Sandbrook in *Molecular Cloning* (1982, Cold Spring Harbor Laboratory, Cold Spring Harbor, New York, pp. 229–246) with the following modifications. Unlabeled deoxyribonucleoside triphosphates were present during first-strand synthesis at 200 µM, poly (A)⁺RNA was used at 50 µg/ml, and reverse transcriptase at 2000 units/ml (obtained from Boehringer Mannheim Biochemicals), and [α-32P]dCTP at 250 µcuries/ml. Additionally, second-strand cDNA was synthesized by the technique of Gubler and Hoffman. (*Gene* 1983, 25:263–269). This procedure employs RNase B and DNA polymerase 1, and has the advantage of generating cDNA libraries from submicrogram quantities of poly (A)⁺ RNA as it eliminates the vector primer system and the classical hairpin loop S1 nuclease cleavage steps, which result in low cloning efficiency.

Nucleotides were removed after the synthesis of the first and second strands of the cDNA by ethanol precipitation and a wash with 70% ethanol. Next, double-stranded cDNA was treated with Eco RI methylase, the latter obtained from New England Biolabs. Phosphorylated Eco RI linkers (pGGAATTCC) also obtained from New England Biolabs were ligated to the double-stranded cDNA in 66 µM Tris pH 7.5, 6.6 µM magnesium chloride, 10 µM dithiothreitol and 1 µM ATP. gt11 DNA was prepared by first ligating the cohesive ends and cutting at the unique Eco RI site. The Eco RI ends were dephosphorylated to prevent spontaneous rejoining with alkaline phosphatase using the conditions described by Maniatis, Fritsch, and Sandbrook in *Molecular Cloning* (1982, Cold Spring Harbor Laboratory, Cold Spring Harbor, New York, pp. 133–134).

Next, 0.5 µg of linker cDNA was ligated to 10 µg of dephosphorylated, Eco RI-cut gt11 with 7 Weiss units of T4 DNA ligase, also obtained from New England Biolabs. The reaction was carried out for 12 hours at 4° C. in a total volume of 10 µl. The ligated gt11 phage was packaged in vitro according to the protocol of the supplier of the packaging kit, which was obtained from Bethesda Research Laboratories. The cDNA phage library was titered on *E. coli* strain Y1088 as described by Young and Davis in *Science* (1983, 22:778–782) on plates containing the chromogenic substance 5-bromo-4-chlor-3-indolyl-β-D-galactopyranoside and 1 mM isopropyl thio-β-D-galactopyranoside (IPTG). Since insertion of DNA sequences into the Eco RI site of gt11 inactivates the *E. coli* Lac Z (β-galactosidase) gene, the proportion of phage carrying cDNA inserts can be determined by plating dilutions of Y1088 in the presence of IPTG and X-gal. Under these conditions, gt11 without inserts produces blue plaques, whereas phage carrying cDNA produce white plaques. Using this method, it was determined that packaging of 1 µg of gt11 DNA ligated to cDNA yields approximately 100,000 recombinant phage, and after amplification of the library on Y1088, the recombinants represented approximately 10% of the total phage population.

Example 2

Identification of cDNA Sequence That Encode molecules with Luciferase Antigenic Determinants.

The gt11 phage library described above was plated on a lawn of *E. coli* strain Y1090 [lac V169 proA⁺lon araD139 strA SupF trpC22:Tn 10(pMC9)], and induced with isopropyl thiol-β-D-galactopyranoside as described by Young and Davis in *Science*, supra. The plate containing the lawn of phage-infected bacteria was overlaid with an inducer-impregnated nitrocellulose filter. Plates containing overlaid filters were incubated at 37° C. for 2 to 8 hours. The position of the filter was marked with a needle so that it could later be realigned with plaques on the dish. The filter was then transferred to a clean petri dish and washed with buffer containing 0.17M NaCl, 0.01M Tris p7.5 (TBS) for 5 minutes. The phage plate from which the filter was taken was stored inverted at 4° C. until needed.

The TBS buffer was removed from the filter and 5 ml of the same buffer plus 3% gelatin with a final pH of 7.5 was added to the filter, and agitated for 15 minutes and drained. Enough TBS buffer containing 3% gelatin, 0.02% azide and 2 µg/ml of IgG specific luciferase antibody was added to each filter, which were then gently shaken overnight to permit the antibody to absorb to luciferase antigenic determinants. Next, the filters were washed for 10 minutes with 10 ml of TBS buffer, then 5 minutes with 10 ml of the same buffer plus 0.05% NP-40, a nonionic detergent, followed by another 10 ml of TBS wash. To each plate containing filters was added 7 ml of TBS plus 3% gelatin, and 5 µl of peroxidase conjugated goat-antirabbit IgG obtained from Bio Rad Corporation. Plates were gently agitated for 1.5 hours to permit sufficient absorption of the peroxidase conjugate to bind to the first antibody and then washed as described above for absorption of the first antibody.

Plaques that adhered to the filters and that exhibit luciferase antigenic determinants were visualized by developing the filters using the chromogenic peroxidase substrate, 4-chloro-1-naphthol. 60 ml of the latter were dissolved in 20 ml of ice-cold methanol, the latter being mixed just before use with 100 ml of TBS containing 60 ul of 30% $H_2O_2$. To each filter was added enough of the developing solution to cover the filter; and generally within 10 to 15 minutes if a particular plaque was positive for luciferase antigenic binding, it exhibited a purple color. Those plaques that exhibited positive staining were located on the phage plates, and removed from the plate using a sterile Pasteur pipette. Phage were eluted from the agar in which they were embedded by transferring them to a solution containing 0.1 molar sodium chloride, 50 mM Tris, ph 7.5, 10 mM magnesium sulfate, 0.01% gelatin, and 2 drops of chloroform, and were allowed to elute overnight at 4° C.

Using the above-described procedures, it is possible to isolate gt11 recombinant phage containing cDNA inserts that encode for protein containing luciferase antigenic determinants.

Example 3

Preparation of Anti-luciferase Antibody.

Firefly luciferase was purified from adult lanterns of *P. pyralis* according to the procedure of Green and McElroy in *Biochemistry Biophysical Acta*, supra. The enzyme was crystallized 4 times and used to immunize New Zealand white rabbits. The antiserum was fractionated using classical ammonium sulfate precipitation techniques at a concentration of 0%–25% and 35%–37%. The resulting pellet obtained from using 35%–37% ammonium sulfate was dissolved in a minimal amount of water and dialyzed against the same. The solution was centrifuged and the pellet discarded. Next, the solution was dialyzed against 0.01 molar of sodium phosphate or Tris-Cl buffer, 0.15 molar sodium chloride, pH 7.8 containing 0.02% sodium azide to inhibit bacterial growth.

Example 4

Expression of cDNA Sequence Encoding Molecules with Luciferase Activity in Procaryotes.

gt11 DNA obtained from plate lysates was partially digested with the restriction endonuclease Eco RI and the cDNA inserts released were isolated by agarose gel electrophoresis yielding inserts ranging in size from 400 base pairs to 1800 base pairs. Isolation of recombinant phage DNA was conducted as described by Maniatis et al., supra. The 1.8 kilobase fragment was ligated into a procaryotic expression plasmid, pKJB824.17. The properties of this plasmid, as well as the conditions needed to propagate it, are described by Buckley in *Ph.D. Thesis* (1985, University of California, San Diego). pKJB8824.17 exhibits the bacteriophage temperature-sensitive repressor $cI_{857}$, and the Rightward promoter, $P_r$, followed by a truncated cro gene exhibiting an Eco RI site. Thus, the homology of the nucleotide bases of the 1.8 kilobase fragment produced by Eco RI cleavage of the recombinant phage permits ligation of the fragment into the Eco RI site of pKJB824.17 resulting in fusion of the reading frames of the truncated cro gene to the 1.8 kilobase cDNA fragment. The resulting novel plasmid is termed pKW101 and is shown in FIG. 1.

pKW101 was transformed into the *E. coli* strain TB1[ara, (lac, propAB), strA Φ80 lacz M15,hsr⁻,hsm⁺] using the calcium precipitation technique described by Maniatis et al., supra. TBI cells containing pKW101 cells were selected by their ability to grow in drug-supplemented media, and then grown up in 10 ml of LB broth containing 10 g of tryptone, 5 g yeast extract, and 5 g sodium chloride per liter with pH 7.4. Cells were grown at 30° C. to an optical density of 0.8.

Next, the expression of luciferase activity was achieved by inactivating the repressor by heating the cells to 45° C. for 30 minutes followed by further incubation for 1 hour at 37° C. Cells were collected by low-speed centrifugation and resuspended in 200 μl of 100 mM $KPO_4$ pH 8.0, 2 mM EDTA, 1 mM dithiothreitol, 0.2 mg/ml protamine sulfate and 1 mg/ml lysozyme on ice for 10 minutes. They were frozen on dry ice and thawed to effect cell lysis and hence liberate molecules with luciferase activity. Aliquots of the cell extract were assayed for luciferase activity by adding 50 μl of the extract to 300 μl of 25 mM glycylglycine buffer pH 7.8, containing 5 mM magnesium chloride and 0.1 mM luciferin. Bioluminescence was ascertained by placing the tubes in luminometer equipped with a chart recorder, and then 100 μl of 20 mM ATP, pH 7, was injected. The intensity of light emission was recorded, a flash of yellow-green light being observed that rapidly decayed to a lower level of luminescence.

To insure that the luminescence observed was due to the expression of inserted cDNA, several controls were run. Luciferin alone added to the cell extract yielded a low level of light, presumably because of endogenous levels of ATP in the cells. In contrast, luciferase activity is not detected in extracts of heat-induced TB1 cells or TB1 cells carrying the vector pKJB824.17 absent cDNA inserts.

Example 5

Construction of Plasmids Useful for Generating Proteins Exhibiting Dual Functions.

Figures 2, 8:
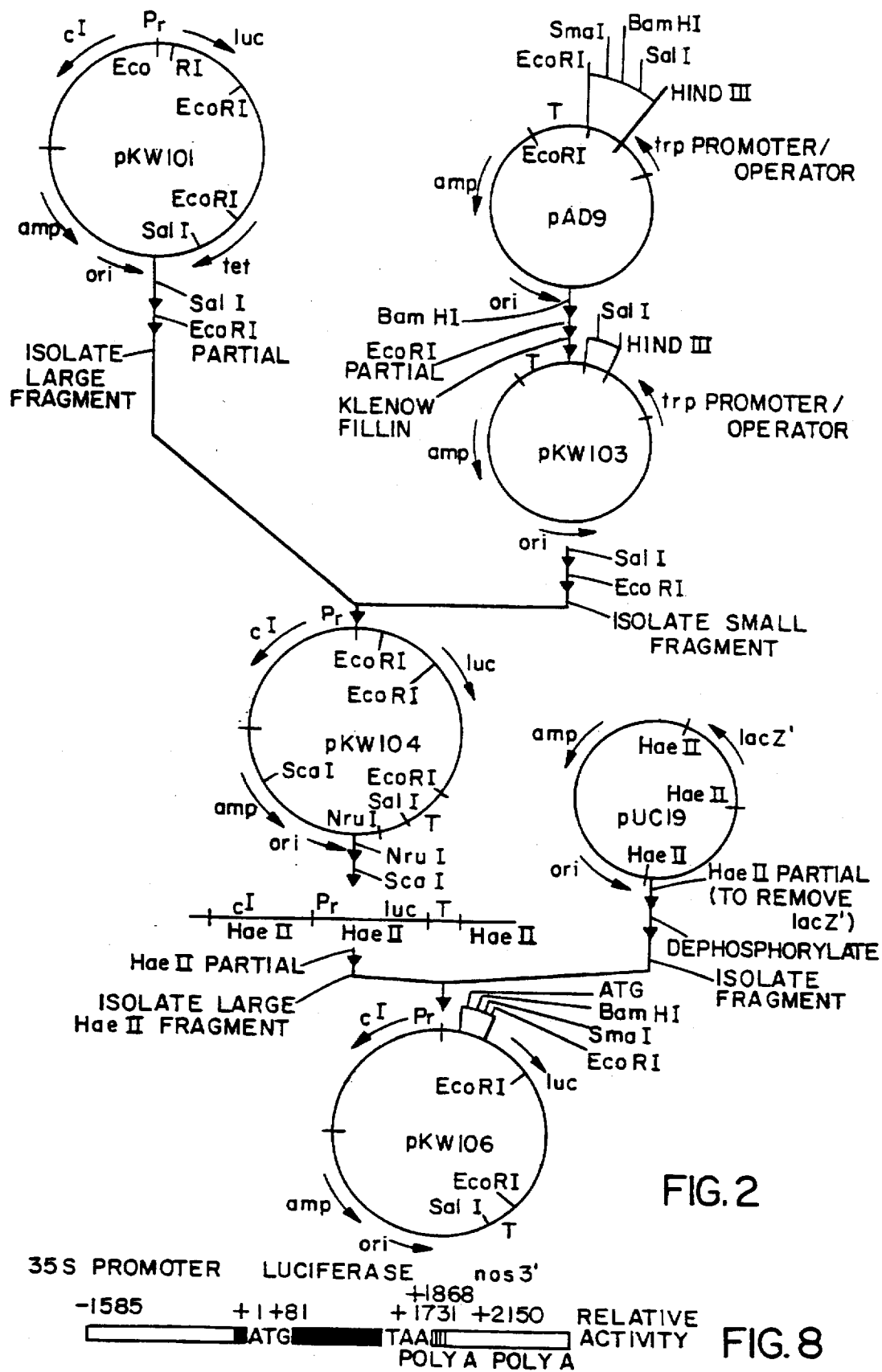
FIG. 2 shows the production of plasmid pKW104 from the plasmids pKW101, pKAD9 and pKW103 and the production of plasmid pKW106 from pKW104 and pUC19.
FIG. 8 shows a DNA cartridge resulting from the fusion of the CaMV35S RNA promoter, luciferase sequences and the 3'-end of the nopaline synthase gene.

Generation of hybrid proteins that exhibit luciferase activity and a second functionality involve engineering a plasmid that permits cloning of functionally distinct DNA sequences adjacent each other that are read in phase. A suitable plasmid, pKW106, can be constructed by treating the plasmid pKW101 with the restriction endonucleases Sal I and Eco RI so as to remove DNA sequences that encode tetracycline resistance in anticipation of inserting therein a transcription terminator sequence derived from another plasmid. Thus, pKW101 minus the region of DNA containing tetracycline-resistance was isolated by agarose electrophoresis. This reaction scheme is shown in FIG. 2. Next, to derive the transcription terminator sequences, the plasmid pAD9 (also shown in FIG. 2) was treated with the restriction endonucleases Bam HI and Eco RI (partial digestion) and then the recessed 3' prime ends created by cleavage with Eco RI and Bam HI were filled in with the Klenow fragment of *E. coli* DNA polymerase 1 as described by Maniatis et al., supra. The resulting plasmid, termed pKW103, was further treated with Sal I and Eco RI and the small restriction fragment exhibiting the transcription terminator isolated by agarose gel electrophoresis.

The large fragment generated from Sal I and Eco RI (partial) digestion of pKW101, and the small fragment generated from pKW 103 containing the transcription terminator were ligated to produce the plasmid, pKW104.

Finally, plasmid pKW106 was generated by treating pKW104 with the restriction endonucleases Nru I and Sca I causing the release of a fragment containing cI, $P_r$, the cDNA insert encoding luciferase activity, the transcription termination sequences, and 3' and 5' regions of plasmid DNA. This fragment exhibits the three Hae II sites—one near cI, a second in the DNA region encoding luciferase activity, and the third downstream of the transcription terminator sequence. This fragment was partially digested with Hae II and inserted into the plasmid pUC 19, which previously was prepared by partial digestion with Hae II cutting to remove the Lac Z gene contained therein. The result is the plasmid, pKW106, shown in FIG. 2.

Several features of pKW106 are worth noting. First, it contains in sequential order restriction endonuclease sites for Bam HI, Sma I and Eco RI immediately downstream of the phage promoter, $P_r$. The DNA region encoding luciferase activity is under control of the phage promoter, $P_r$, and is adjacent the transcription terminator region. Further, the plasmid carries the gene for ampicillin resistance. The restriction sites Bam HI and Sma I are particularly useful in that they are unique and provide sites for inserting cDNA to produce hybrid protein molecules that exhibit luciferase activity plus a second biological activity. Eco RI can also be used for this, but is not unique and requires partial digestion.

Example 6

Construction of Plasmids Exhibiting DNA Sequence Encoding Hybrid Proteins.

Representative members of two types of plasmids that have been constructed to date that express hybrid protein molecules will be described.

a. Hybrid Proteins Exhibiting Modified Luciferase Bioluminescene.

Figure 3:
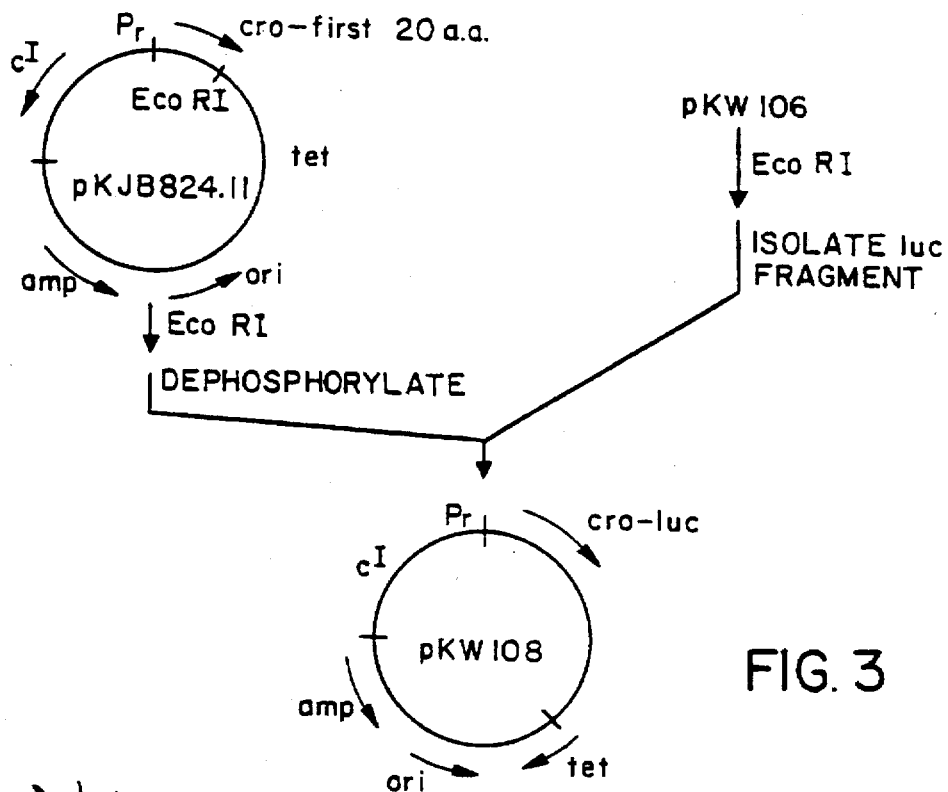
FIG. 3 is a schematic diagram of the production of plasmid pKW108, a cro-luc construct, from the plasmid pKJB824.11 and pKW106.

The plasmid pKW106 was produced as described in Example 5 and treated with Eco RI to release the DNA insert containing the sequence encoding luciferase activity. The sequence was isolated using standard techniques and ligated to the plasmid, pKJB824.11, produced as described by Buckley, supra, after the latter was cut with Eco RI and dephosphorylated with calf intestine alkaline and phosphatase to prevent recirculization and subsequent ligation without a DNA insert. The result is plasmid pKW108 which is shown in FIG. 3.

When pKW108 is transformed into a suitable strain of *E. coli*, it expresses a hybrid protein consisting of 20 amino acids of the cro gene, with the remainder being derived from the DNA sequences encoding luciferase activity. When extracts of cells containing pKW108 are assayed for bioluminescence as described in Example 4, an initial flash of light is observed, which decays rapidly to 40% of the maximum intensity. Surprisingly, there then follows a period wherein the intensity of light emitted remains constant until the luciferin substrate is depleted. This long-lived period of light emission should be compared with the near instantaneous and complete decay of bioluminescence effected by native luciferase.

Figure 4:
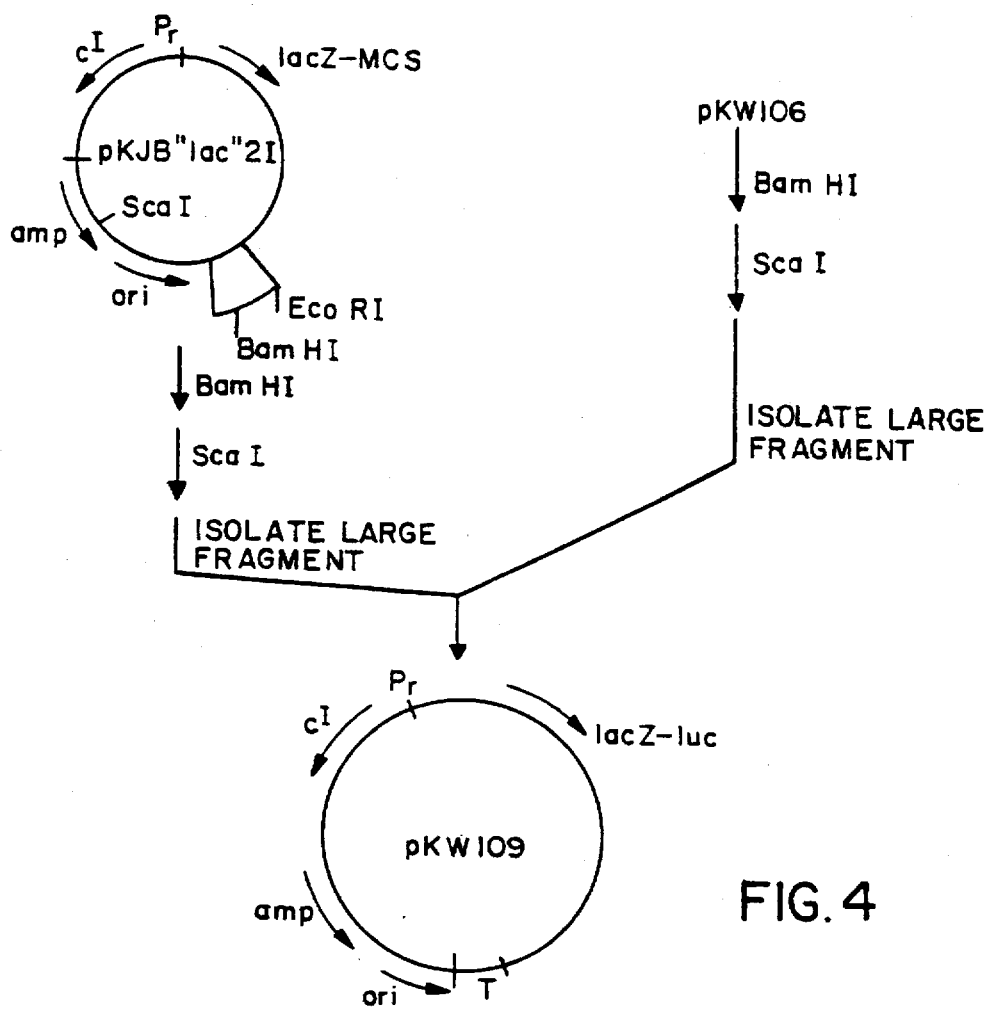
FIG. 4 is a schematic diagram of the production of plasmid pKW109 from plasmids pKWJB"Lac" ZI and pKW106.

Representative of a class of plasmids that express hybrid molecules that exhibit two distinct biological activities is pKW109. This plasmid contains DNA that encodes a hybrid protein exhibiting luciferase activity. FIG. 4 shows the steps taken to generate pKW109. The plasmid pKW106 described in Example 5 was restricted with Bam HI and Sma I, and the large fragment containing the DNA sequences, including luciferase activity and the transcription terminator, were isolated. Next, the plasmid pKJB lac ZI was cut with Bam HI and Sca I. Restriction with Bam HI and Sca I liberates a fragment with cI, Pr and the Lac Z-inc5 DNA sequences. The latter was ligated to the Bam HI/Sca I DNA fragment produced from pKW106 to yield pKW109.

Expression of pKW109 in a suitable strain of a *E. coli* can be expected to yield a protein with one enzymatic activity and luciferase, both of which are assdyed by techniques described herein, or well-known in the art. pKW109 demonstrates that a large peptide can be fused to uc without destroying bioluminescent activity. Thus fusions with two enzymatic activities are feasible.

Example 7

Immunoassay Employing Hybrid Luciferase Molecules

Representative of the types of assays that hybrid molecules that exhibit luciferase can be employed in are solid-phase immunochemical binding assays to detect antigenic substances in biological fluids. Thus, it should be possible to determine the presence of β-galactosidase using the hybrid molecule, exhibiting luciferase enzymatic activity and β-galactosidase antigenic activities generated in Example 6. This can be accomplished by raising antibodies to β-galactosidase; either polyclonal or monoclonal antibodies can be utilized. Polyclonal antibodies can be generated in rabbits and purified by standard ammonium sulfate precipitation procedures, whereas mouse monoclonal antibodies can be prepared by the procedure of Kohler and Milstein as described in *Nature* (1975, 256:495–497). Antibodies so obtained are affixed to solid support surfaces using techniques well-known in the art, cellulose or agarose beads being suitable for this purpose. Preparation of the beads by cyanogen bromide activation and subsequent β-galactosidase antibody coupling is carried out as described Wide in *Methods of Enzymology* (1981, 73:203–224). Next, beads containing coupled antibody are added to test tubes with a suitable buffer, and a cell extract or other source of fluid containing an unknown amount of β-galactosidase, and the luciferase β-galactosidase hybrid molecule added. The reactants are allowed to compete for binding to antibody bound to the bead for 1 hour at 37° C., then the beads separated from unbound reactants by centrifugation. After washing the beads with a suitable buffer to remove residual amounts of unbound reactants, the amount of β-galactosidase present in the cell extract is determined by assaying the intensity of bioluminescence generated from the luciferase moiety bound indirectly to the beads by attachment of the β-galactosidase region to the antibody. This is accomplished by performing a luciferase assay as described in Example 1 and monitoring light intensity. Light intensity is related to β-galactosidase concentration in the cell extract by simultaneously constructing a standard curve by repeating essentially the same assay but using a known amount of β-galactosidase, and determining the concentrations of β-galactosidase needed to successfully compete with the hybrid molecule to yield a particular level of light emission. The procedures, buffers, and reaction conditions necessary to carry out these assays is further described by Wide in *Methods of Enzymology*, supra.

Example 8

Construction of a Genomic Library from *P. pyralis*.

Figure 5:
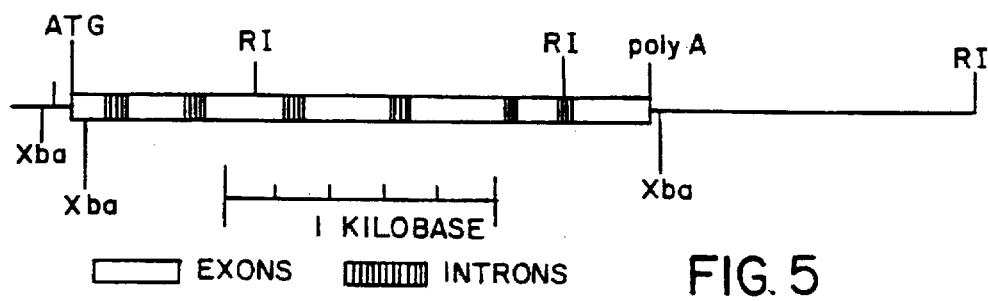
FIG. 5 is a restriction map of the luciferase gene isolated from a genomic library.

DNA from *P. pyralis* was isolated from frozen beetles by grinding the same in a mortar and pestle. 50 mM Tris, pH 8, and 10 mM EDTA were added and proteinaceous material digested with proteinase K in the presence of 1% sodium dodecyl sulfate (SDS). DNA was twice extracted, once with phenol-chloroform and a second time with chloroform, and precipitated with ethanol and redissolved in TBS buffer. The DNA was subsequently purified by banding on an ethidium bromide-cesium chloride equilibrium gradient. After isolating the same from the gradient, DNA was subjected to partial digestion with the restriction endonuclease Sau3A. Fragments ranging in size from 12–20 kilobases were isolated by centrifugation on a sucrose-density gradient. These fragments were ligated to the vector EMBL4 DNA, which was previously digested with Bam HI. This phage mixture was packaged using in vitro packaging extracts, which are commercially available form Bethesda Research Laboratories or Vector Cloning Systems. Packaged phage were then plated on a lawn of *E. coli* cells, strain LE392, and plaques so obtained were screened by the filter hybridization method of Benton and Davis as described in *Science* (1977, 191:180–182). The probe used to detect plaques harboring luciferase DNA sequences was a 5' Eco RI fragment obtained from the cDNA library discussed in Example 4. This probe, termed Luc23, was labeled with $^{32}$P by nick-translation as described by Rigby, Diekman, Rose, and Berg in *Journal of Molecular Biology* (1977, 113:237–251). Plaques were detected that hybridized to the Luc23 cDNA probe, and these were purified by standard techniques. All the clones obtained contained three Eco RI fragments that were homologous to the luciferase Luc23 cDNA probe. A restriction map of the luciferase gene is shown in FIG. 5.

Example 9

Figure 6:
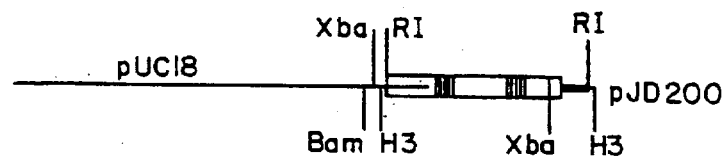
FIG. 6 is a restriction map of the plasmid pJD200.
Figure 7:
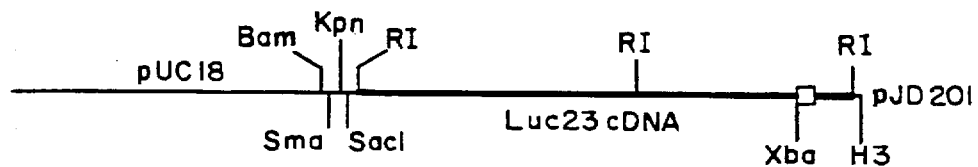
FIG. 7 is a restriction map of the plasmid construct pJD201 (not to scale), in which H3=HindIII, RI=Eco RI and Bam=Bam HI.

Construction of Vectors Suitable for expressing luciferase activity in eucaryotic cells To obtain expression of luciferase activity in eucaryotic cells, a hybrid DNA molecule was constructed consisting of Luc23 cDNA and genomic DNA. This was accomplished by purifying the 5' Eco RI fragment from the genomic clone obtained as described in Example 8. The procedure entailed using Eco RI to obtain the fragment, making it necessary to fill in the Eco RI sites to create blunt ends prior to ligating Hind III linkers to the termini of the fragment. Next, the Hind III-linkered fragment was inserted into a Hind-III site of the plasmid vector pUC13 to yield the plasmid pJD200. A restriction map of pJD200 is shown in FIG. 6. Digestion of pJD200 with XbAI releases all but the 5'-most sequences of the luciferase genomic DNA from the vector. Thus, when pJD200 was digested with Bam HI and XbAI, it was possible to isolate the fragment consisting of the vector plus the 5'-most portion of the luciferase gene. This fragment was ligated to a Bam HI-XbAI fragment composed of luciferase cDNA extending from the same XbaI site that was present in the genomic DNA to the end 3' of the Luc23 cDNA to yield the plasmid pJD201. Unlike the Luc23 cDNA, which lacks an initiation codon, pJD201 has the natural luciferase translational start and polyadenylation site. Plasmid pJD201 is shown in FIG. 7. It should be noted that the Luc23 cDNA/genomic insert of pJD201 is suitable in use with a wide variety of vectors that may be expressed in eucaryotes and procaryotes. Further, it should be noted that the hybrid DNA molecule can also be utilized for expressing luciferase activity in plant cells.

Example 10

Example of Luciferase Activity in Eucaroytic Cells.

The Hind III-Bam HI DNA fragment exhibiting luciferase sequences was obtained from pJD201 described in Example 9 using the same enzymes, and was inserted downstream from an SV 40 promoter in the plasmid pBR322-based vector pSV2. The new construct, termed plasmid pSV2$_L$, was introduced into CV 1 monkey cells by the calcium phosphate DNA precipitation technique. After 48 hours, cells were harvested and lysed by three cycles of freezing and thawing in 0.1 molar potassium phosphate (KPO$_4$), pH 7.8, containing 1 mM dithiothreitol. The cell extracts were assayed for luciferase activity as described in Example 4. Western blot analysis revealed that the hybrid DNA construct, Luc23 cDNA-genomic DNA, synthesizes native luciferase.

Example 11

Construction of Vectors Suitable for Expressing Luciferase Activity in Plant Cells A pUC19 derived plasmid suitable for expressing luciferase activity in plant cells was constructed comprising a DNA cartridge consisting of a plant virus promotor (CaMV [cauliflower mosaic virus]35S RNA promoter), luciferase cDNA coding sequences and polyadenylation site sequences.

Plasmid pJD201, described in Example 9, was the source of luciferase cDNA coding sequences. pJD201 was treated with the restriction enzymes Hind III and Bam HI, and the resulting Hind III-Bam HI fragment containing sequences encoding luciferase was isolated by standard techniques after which the upstream Hind III site was filled in converted to a Bam HI site by the addition of Bam HI linkers. The procedures for achieving these steps are standard and are well known to those skilled in the art; see, for example, Maniatis et al, supra.

The plant virus (CaMV) promoter was ligated to the Hind III-Bam HI fragment on the upstream side of the luciferase cDNA coding sequences. The promoter was the 35S RNA promoter obtained from cauliflower mosaic virus. The promoter was isolated from a plasmid, pCaM10, which is described by R. C. Gardner et al in *Nucleic Acids Research*, Volume 9, page 2871, (1981). In order to ligate the 35S RNA promoter to the luciferase sequences, a Bam HI site was introduced at the normal start of transcription by oligonucleotide-directed mutagenesis of pCaM10. Using well established mutagenesis techniques, the nucleotide sequence GGACAC was converted to GGATCC. The underline indicates position 7431 which is believed to be the start of 35S RNA transcription as shown by Covey et al in *Nucleic Acids Research*, Volume 9, page 6738, (1981) and Guilley et al in *Cell* Volume 30, page 763, (1982).

Next, plant polyadenylation sequences were fused to the downstream side of the luciferase DNA sequences. The latter were added to stabilize luciferase mRNA. This consisted of isolating a 1,028 base pair fragment containing polyadenylation sites from the 3' end of the nopaline synthase (nos) gene. The 3' fragment of the nos gene was obtained from the plasmid, pNCAT4.

FIG. 8 shows the DNA cartridge resulting from the fusion of the CaMV 35S RNA promoter, luciferase sequences and the 31-end of the nopaline synthase gene. Also shown in FIG. 8 is the sequence ATG which is about 81 bases downstream from the Bam HI site linking the 35S RNA promoter and the luciferase sequences. This site is thought to be the translation start site. Also note that 3' of the luciferase coding sequences there exists a Ssp I-Bam HI fragment derived from the firefly that has a consensus polyadenylation signal. It is located about 28 bases upstream from the 3' end of the luciferase sequences. The structure shown in FIG. 8A denotes the plasmid pDO432.

Figure 9:
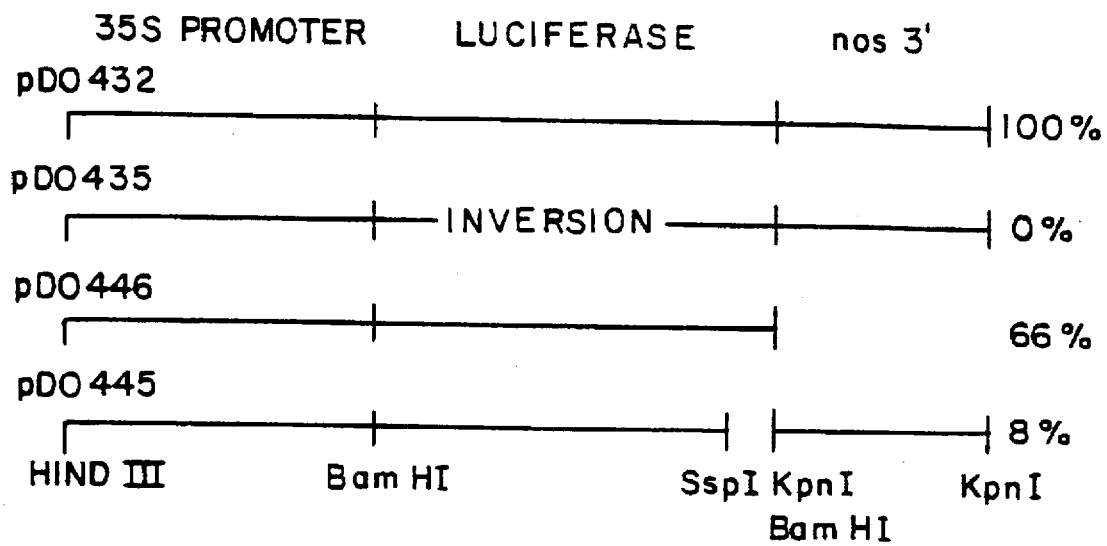
FIG. 9 shows the effect of deleting, or inverting, DNA from the DNA cartridge shown in FIG. 8 on luciferase activity.

FIG. 9 shows pD0432 and a construct pD0435 that have the luciferase sequences inverted. pD0435 does not produce luciferase activity.

pD0432 was tested for luciferase activity after electroporation into cultured carrot cell protoplasts. Electroporation was carried out using the techniques essentially described by Fromm et al in the Proceedings of the National Academy of Sciences U.S.A., Volume 82, page 5824, (1985). Cultured carrot cell protoplasts were made from a suspension culture line from Daucus Carota W001. About 10 micrograms of pD0432, and 500 micrograms of carrier calf thymus DNA were combined and electroporated into protoplasts. Next, carrot extracts were prepared 24 hours after electroporation by repeated freeze-thawing of about $0.5 \times 10^7$ to $1 \times 10^7$ carrot cells. The freeze-thawing procedure was performed in a buffered solution (pH of 7.5) that contained 100 mM potassium phosphate buffer and 1 mM dithiothreitol. The extract was centrifuged for five minutes in a microfuge (Eppendorf) at 4 degrees Centigrade. The resulting supernatant fluid was assayed for luciferase activity wherein about 1/10 of the volume of the fluid was diluted into about 400 microliters of assay buffer which comprised 14 mM glycylgylcine buffer (pH 7.8), 14 mM MgCl$_2$ and 6 mM ATP. To this solution was added 100 microliters containing 1 mM of the luciferase substrate luciferin. Light emission was measured in a luminometer (LKB, Model 1250). It was observed that the carrot extract produced a light flash in the presence of luciferin and ATP.

Example 12

Relative Polyadenylation Site Contribution

The 3'-end of the nopaline synthase (nos) gene provides polyadenylation sites; however, since additional polyadenylation sites are also present at the 3' end of the pJD201 Hind III-Bam HI fragment experiments were done to ascertain the relative contributions of the plant (nopaline synthase, nos) and the endogenous firefly polyadenylation sites to the expression of the luciferase gene. It was anticipated that there would be a loss of activity if the nos gene sequences were deleted from the construct, presumably because these sequences stabilize messenger luciferase RNA. FIG. 9 shows that this is indeed the case; there is approximately a 34% reduction in luciferase activity if the nos 3'-fragment is deleted. Nonetheless, it is important to note that a construct lacking the polyadenylation nos sites nevertheless produces significant amounts of luciferase as measured by light emission. The DNA construct lacking the nos gene sequences is termed pDO 446.

The Hind III-Bam HI fragment containing the sequences encoding luciferase also exhibits polyadenylation sites at the 3' end of the luciferase sequences. Thus, another construct was generated that had these sequences deleted to determine their effect on luciferase expression. This was accomplished using the restriction enzymes Ssp I and Bam HI; these enzymes remove a 139 base pair fragment having the polyadenylation sites. A substitute 139 base pair fragment was then spliced to the construct to replace the polyadenylation sites yielding the plasmid pD0445, shown in FIG. 9. pDO445 has the CAMV 35S promoter sequences, luciferase sequences less its 3' polyadenylation sites and the nos 3' polyadenylation sequences. Luciferase activity was measured as described above, and it was observed that there was a 92% decrease in luciferase activity relative to pDO 439.

The marked reduction in luciferase activity resulting from the deletion of polyadenylation sites associated with the 3' end of the luciferase sequences was unexpected. It will be appreciated by those skilled in the art that this finding suggests that modifications to the polyadenylation regions can be expected to yield a family of plasmids having intermediate luciferase activities.

Example 13

Production of Stable Plant Transformants Expressing Luciferase Activity

Stable plant transformants harboring the plasmid pDO432 were produced by inserting pDO432 described in Example 11 at the Hind III site in the Ti plasmid of the bacterium Agrobacterium tumefaciens. The Ti plasmid used was the bacterial vector bin-19, and is described by Bevan in *Nucleic Acids Research* Volume 12, page 8711, (1984). The Ti plasmid containing pDO432 was transferred by conjugation into the Agrobacterium tumefaciens strain GV3111. The latter strain carries the helper plasmid pTiB6S3SE, and is described by Horsch et al in *Science* Volume 227, page 1229, (1985). Nicotiana tabacum plants (Wisconsin-38 Cultivar) were inoculated with the bacterial vector by the leaf disk inoculation method as described by Horsch et al (above) and kanamycin resistant transformants were selected and shown to express luciferase activity by grinding a portion of a leaf and assaying the leaf for luciferase activity. The assay was performed essentially as described in Example 11.

Figure 10:
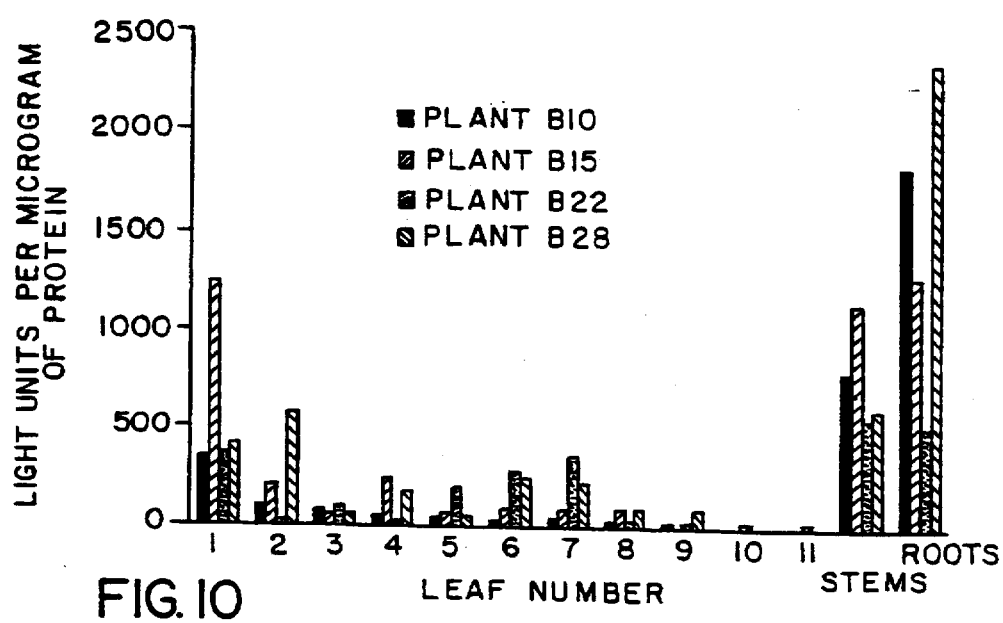
FIG. 10 is a graph of luciferase activity measurements from various plant transformants.

FIG. 10 shows luciferase activities measured from the transformants designated B10, B15, B22, and B828. "Leaf Number" is the position of the leaf on the plant, starting with the younger leaves at the top of the plant and progressing to the older leaves at the bottom. The Figure particularly reveals that while luciferase activity is present in extracts from all plant organs, that is, leaves, roots and stems, the amount of activity expressed by these organs varies considerably. That this activity is due to luciferase encoded by the Hind III-Bam HI fragment was shown by protein blots of leaves from B15 which revealed a 62 kilodalton protein that reacted with luciferase antiserum.

Figure 11:
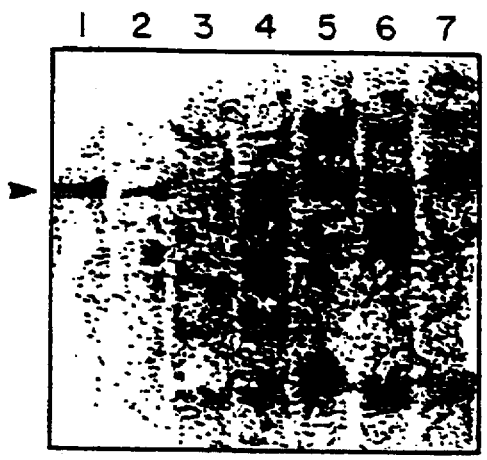
FIG. 11 shows DNA blotting results from various transgenic tobacco plants.

To confirm that the luciferase activity measured in the plant organs resulted from the of pDO432 inserted into the plant genome, genomic DNA blots of the plants were performed. FIG. 11 shows a blot from the transgenic tobacco plants B10,B15,B22, and B828 resulting from cutting plant extracted DNA with Hind III. The DNA was fractionated on a 1% agarose gel, and transferred to a nitrocellulose filter followed by hybridization with a radioactive labeled (nick translated) 1.6 kb Hind III-Bam HI fragment obtained from pDO432 that contains the cauliflower mosaic virus 35S RNA promoter. The procedures for the genomic blots are described by Maniatis et al in *Molecular Cloning A Laboratory Manual*, Cold Spring Harbor Laboratory, Cold Spring Harbor, N.Y. (1982).

Lanes 4–7 of FIG. 11 present blots of plants B10, B15, B22, and B28 respectively. Lane 3 shows a control blot taken from a tobacco plant that was not inoculated with Ti plasmid. Lanes 1 and 2 in the Figure show copy number standards. The arrow marks the position of a 7 kilobase fragment that arises from Hind III cleavage of integrated pDO432 DNA. With the exception of the control blot, all the blots exhibit the 7 kilobase fragment. These findings establish that pDO0432 has been incorporated into the transgenic tobacco plants.

Example 14

Visualization of Luciferase Activity in Transgenic Tobacco

Figure 12:
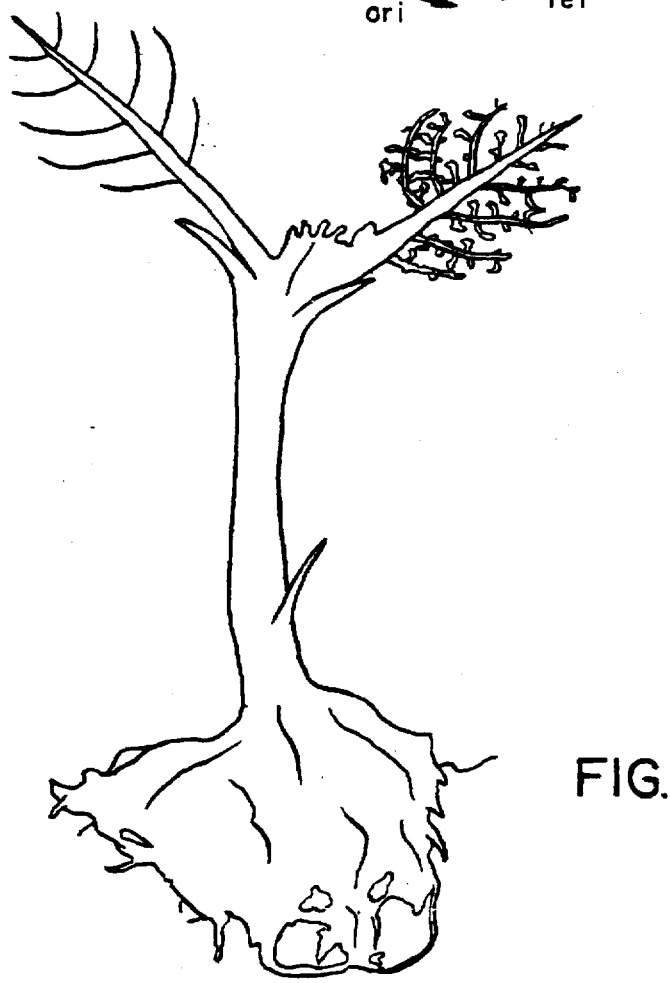
FIG. 12 shows the luminescent profile of a transgenic tobacco plant incubated with luciferin coupled with detection of lighted emission using common photographic techniques.

A transgenic tobacco plant, B21, harboring pDO432 was watered for 6 hours with 5 milliliters of a 1 mM luciferin solution (pH 5.0) containing 100 mM sodium citrate and 20% dimethyl sulfoxide. Light was detected by contacting the plant to Kodak Ektachrome 200 film (4 by 5 inch sheet) for 24 hours. FIG. 12 shows that the pattern of light emission tends to be intense from the roots, stems and young upper leaves.

Example 15

Plasmids that Express Hybrid Proteins of Proteins A and Luciferase.

Two plasmids were created that express protein A-luciferase hybrid molecules. The first plasmid, pKW118-2, was constructed from pKW111, which is similar to pKW106 described in Example 5 but lacking most of the 3' non coding region of the luciferase cDNA. That is, the region from the SspI site clockwise to the terminal EcoRI site was replaced by an XhoI linker using techniques known to those skilled the art. This plasmid, pKW111, was cleaved at the BaM HI site, which resides immediately downstream of the translational initiation for Luc and the ScaI site in the amp gene. Next, the fragment containing the luc gene was ligated to a fragment of a commercially available plasmid sold by Pharmacia, pRIT2T which contains the DNA sequences coding for protein A (spa). The fragment containing the spa gene was generated by clevage at Bam HI site located in the spa gene and an analagus ScaI site in the amp gene. Ligation was achieved using reagents and reaction conditions well known to those skilled in the art. The resultant plasmid, pKW118-2, has the coding sequence of a modified protein A ligated to the 5' end of the luc gene originally expressed in the pKW101 plasmid described in Example 4.

The second plasmid capable of expressing hybrid protein A-luciferase molecules, pKW118-10, was constructed in a fashion similar to pKW118-2 except that the source of the luc gene was a plasmid term pKW112-73 instead of pKW111. The latter plasmid is lacking the coding sequence for the first six N-terminal amino acids of luciferase. In contrast, pKW112-73 has this coding sequence except for the initial methionine. The latter amino acid is replaced by a Bam HI site. The plasmid pKW112-73 was constructed by first cleaving plasmid pJD206 at the unique linker site just 5' of the natural translation and initiation site of luc, and subsequently degrading 3' DNA with Bal-31 exonuclease. Next, the DNA was treated with XbaI to cut the XbaI site within the luciferase gene, and the resulting small fragment isolated. The fragment was ligated into pKW111 that had previously been treated with Bam HI and XbaI, yielding in a small fragment that was removed. This treatment of pKW111 resulted in a family of plasmids similar to pKW111 except that the BamHI site was positioned at various positions near the native translation initiation. The resulting family of plasmids was screened for enzymatic activity in vivo and by DNA sequencing of the 5' end of luc to ultimately yield the plasmid pKW112-73. The latter plasmid, as stated above, contains the complete coding sequence for luciferase except for the replacement of the translational initiator (Met) by a unique restriction site to allow for gene fusion.

Both plasmids, pKW118-2 and pKW118-10, express hybrid proteins exhibiting the functional properties of both halves of the gene fusion. That is, they express proteins that bind to antibodies, and that are is luminescent. It is worth noting that the hybrid protein produced by pKW118-10 is distinct from that of pKW118-2 and in that it is more stable, especially in low ionic strength buffers.

It will be appreciated that the experimental conditions employed to realize both of the plasmids described above, as well as the expression of their protein products can be realized using materials and assay methods either described in the previous examples, or that are well known to those skilled in the art.

It will be apparent to those skilled in the art that there are numerous variations in the actual processes and materials which are not described herein by which are clearly within the scope and spirit of this invention. Therefore, the above description and examples should be considered as instructional only and the invention is to be limited only by the appended claims.

We claim:

1. A method for producing hybrid proteins which comprises expressing in a procaryotic or eucaryotic cell, a lysate, of said cell or a cell-free protein translation system, a first recombinant DNA sequence coding for Coleoptera luciferase;

expressing a second DNA sequence coding for a second polypeptide having an activity different from that said Coleoptera luciferase, and causing transcription and subsequent translation of said first and second DNA sequence as a unit to yield said hybrid protein translation product which catalyzes the oxidation of Coleoptera luciferin to yield light and which also expresses said other activity.

2. A method as in claim 1 wherein the second polypeptide has binding activity.

3. A method as in claim 1 wherein the second polypeptide has antigenic activity.

4. A method as in claim 1 further comprising using said hybrid protein as an indicator of genetic activity.

5. A method as in claim 1 further comprising using said hybrid protein as a bioluminescent reporter molecule.

6. A method as in claim 1 further comprising using said hybrid protein as an indicator of the presence of a ribonucleoside triphosphate.

7. A method as in claim 6 wherein said ribonucleoside triphosphate is adenosine triphosphate or guanosine triphosphate.

8. A method as in claim 1 wherein said Coleoptera luciferase comprises luciferase of an insect selected from the families Lampyridae and Elateridae.

9. A Method as in claim 8 wherein said Coleoptera luciferase comprises luciferase of an insect selected from the genius Photinus.

10. A method as in claim 9 wherein said Coleoptera luciferase comprises luciferase of the species *Photinus pyralis*.

11. A method for producing hybrid proteins which comprises:

expressing in a procaryotic or eucaryotic cell, a lysate of said cell or a cell-free protein translation system, a first recombinant RNA sequence coding for Coleoptera luciferase;

expressing a second RNA sequence coding for a second polypeptide having an activity different from that of said Coleoptera luciferase, and causing translation of said first and second RNA sequences as a unit to yield said hybrid protein translation product which catalyzes the oxidation of Coleoptera luciferin to yield light and which also expresses said other activity.

12. A method as in claim 11, wherein said light is an indicator of the expression of said RNA.

13. A method as in claim 12, wherein said light resulting from the expression of said RNA is an indicator of the presence of a ribonucleoside triphosphate.

14. A method as in claim 13 wherein said ribonucleoside triphosphate adenosine triphosphate or guanosine triphosphate.

15. A method as in claim 11 wherein said Coleoptera luciferase comprises luciferase of an insect selected from the families Lampyridae and Elateridae.

16. The method of claim 15 wherein said Coleoptera luciferase comprises luciferase of an insect selected from the genus Photinus.

17. The method of claim 16 wherein said Coleoptera luciferase comprises luciferase of the species *Photinus pyralis*.

* * * * *

UNITED STATES PATENT AND TRADEMARK OFFICE
CERTIFICATE OF CORRECTION

PATENT NO.  : 5,674,713
DATED       : October 7, 1997
INVENTOR(S) : Marlene DeLuca McElroy, et al.

It is certified that error appears in the above-indentified patent and that said Letters Patent is hereby corrected as shown below:

Column 3, line 56;
column 4, lines 9, 13, 15, 18, 19, 22, 43 and 64;
column 5, lines 27, 33 and 64;
column 7, line 2;
column 9, lines 37, 45, 48, 57, 61 and 64;
column 10, lines 5 and 55;
column 11, line 14: replace "gt11" with -- λgt11 --.

Column 13, between lines 21 and 22, insert:

--b. Hybrid Protein Molecules That Exhibit Luciferase
    and a Second Enzymatic Activity--.

Column 20, claim 14, line 45, between "triphosphate" (first occurrence) and "adenosine," insert --is--.

Signed and Sealed this

Ninth Day of June, 1998

Attest:

BRUCE LEHMAN

*Attesting Officer*    *Commissioner of Patents and Trademarks*